(12) United States Patent
MacMillan

(10) Patent No.: US 8,701,655 B2
(45) Date of Patent: Apr. 22, 2014

(54) CHIN STRAP ASSEMBLY FOR SLEEP APNEA

(76) Inventor: Russell J. MacMillan, SW Ranches, FL (US)

( * ) Notice: Subject to any disclaimer, the term of this patent is extended or adjusted under 35 U.S.C. 154(b) by 310 days.

(21) Appl. No.: 13/236,354

(22) Filed: Sep. 19, 2011

(65) Prior Publication Data

US 2012/0067351 A1   Mar. 22, 2012

Related U.S. Application Data

(60) Provisional application No. 61/384,173, filed on Sep. 17, 2010.

(51) Int. Cl.
*A61M 15/00*  (2006.01)
*A62B 7/00*  (2006.01)

(52) U.S. Cl.
USPC .................... 128/202.13; 128/200.24; 602/74

(58) Field of Classification Search
USPC ............ 128/207.11, 207.13, 207.17, 200.24, 128/201.22, 201.23, 201.29, 202.18, 128/202.19, 204.18, 206.24, 206.21, 128/202.13; 602/74
See application file for complete search history.

(56) References Cited

U.S. PATENT DOCUMENTS

| 5,361,416 | A  | * | 11/1994 | Petrie et al. ................... 2/171.2 |
| 6,470,886 | B1 | * | 10/2002 | Jestrabek-Hart ......... 128/207.11 |
| 7,188,620 | B2 | * | 3/2007 | Amarasinghe ........... 128/201.22 |
| 7,766,199 | B1 | * | 8/2010 | Caperon ....................... 224/160 |
| 2007/0181135 | A1 | * | 8/2007 | Baker .......................... 128/848 |
| 2008/0115788 | A1 | * | 5/2008 | Eschen et al. ............ 128/207.11 |
| 2010/0258136 | A1 | * | 10/2010 | Doherty et al. .......... 128/207.17 |

* cited by examiner

*Primary Examiner* — Justine Yu
*Assistant Examiner* — Colin W Stuart
(74) *Attorney, Agent, or Firm* — Laurence A. Greenberg; Werner H. Stemer; Ralph E. Locher

(57) ABSTRACT

A chin strap assembly that easily helps in keeping the mouth closed in conjunction with a respiratory machine. The chin strap assembly includes a main body having a center, a first strap protruding from a first side of the center, and a second strap protruding from a second side of the center. The first strap and the second strap are separated by a gap. The main body is made of an inner layer surrounded by an outer layer. The outer layer is made of a soft material and the inner layer is made of a stuffing material.

10 Claims, 1 Drawing Sheet

CHIN STRAP ASSEMBLY FOR SLEEP APNEA

CROSS-REFERENCE TO RELATED APPLICATIONS

This application claims the benefit of priority to U.S. Provisional Application No. 61/384,173 filed Sep. 17, 2010, the contents of which are incorporated herein by reference.

BACKGROUND OF THE INVENTION

The present invention generally relates to a head strap assembly. More particularly, the present invention relates to a chin strap assembly to be used with a respiratory mask.

Sleep apnea occurs when air cannot flow into or out of the patient's nose or mouth during sleep. People having sleep apnea stop breathing for short periods of time during sleep, reducing the quality and depth of their sleep. In addition, people having sleep apnea tend to mouth-breath during sleep which may cause the jaw to drop. It is common for patients having sleep apnea problems to use a Continuous Positive Airway Pressure device (CPAP) or a Bi-level Positive Airway Pressure device (BiPAP) while sleeping. The use of these devices requires the patient to wear a respiratory mask over the nose during sleep in order to force air through the nasal passages. Unfortunately, the respiratory masks allow the air to escape from the mouth and are also difficult to keep on the patient's nose. Furthermore, the respiratory masks do not prevent the jaw of the patient from dropping.

As can be seen, there is a need for an accessory that easily helps in keeping the respiratory mask in place.

SUMMARY OF THE INVENTION

In one aspect of the present invention, a chin strap assembly includes a main body having a center, a first strap protruding from a first side of the center, and a second strap protruding from a second side of the center; the first strap and the second strap are separated by a gap; the main body is made of an inner layer surrounded by an outer layer; the outer layer is made of a soft material and the inner layer is made of a stuffing material.

In another aspect of the present invention, a method for treating a sleep apnea patient comprising the steps of: covering the mouth of the patient with a chin strap assembly including a main body having a center, a first strap protruding from a first side of the center, and a second strap protruding from a second side of the center; wherein the first strap and the second strap are separated by a gap; wherein the main body is made of an inner layer surrounded by an outer layer; wherein the outer layer is made of a soft material and the inner layer is made of a stuffing material; wrapping the first strap to the back of the head of the patient; passing the second strap under the chin of the patient, then lifting the second strap to cover the ears of the patient, and then securing the second strap to the top of the head of the patient; and placing a respiratory mask over the nose of the patient.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a chin strap assembly that easily helps in keeping the mouth closed in conjunction with a respiratory machine.

Figure 1:
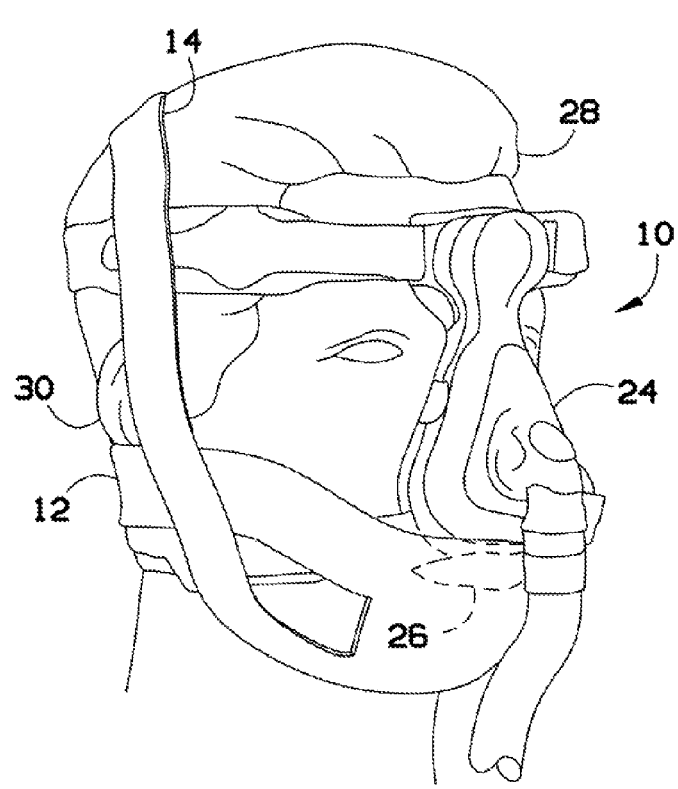
FIG. 1 illustrates a chin strap according to an exemplary embodiment of the present invention showing the chin strap in use.
Figure 3:
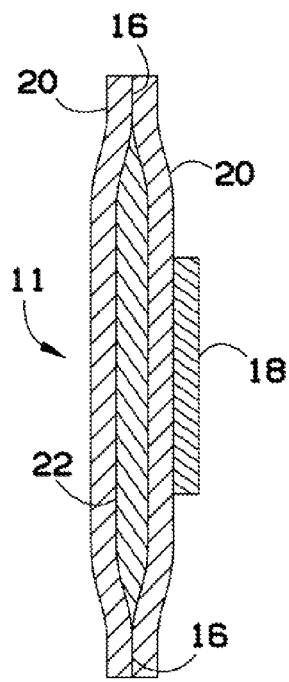
FIG. 3 illustrates a cross-sectional view of the chin strap assembly taken along line 3-3 in FIG. 2.
Figure 2:
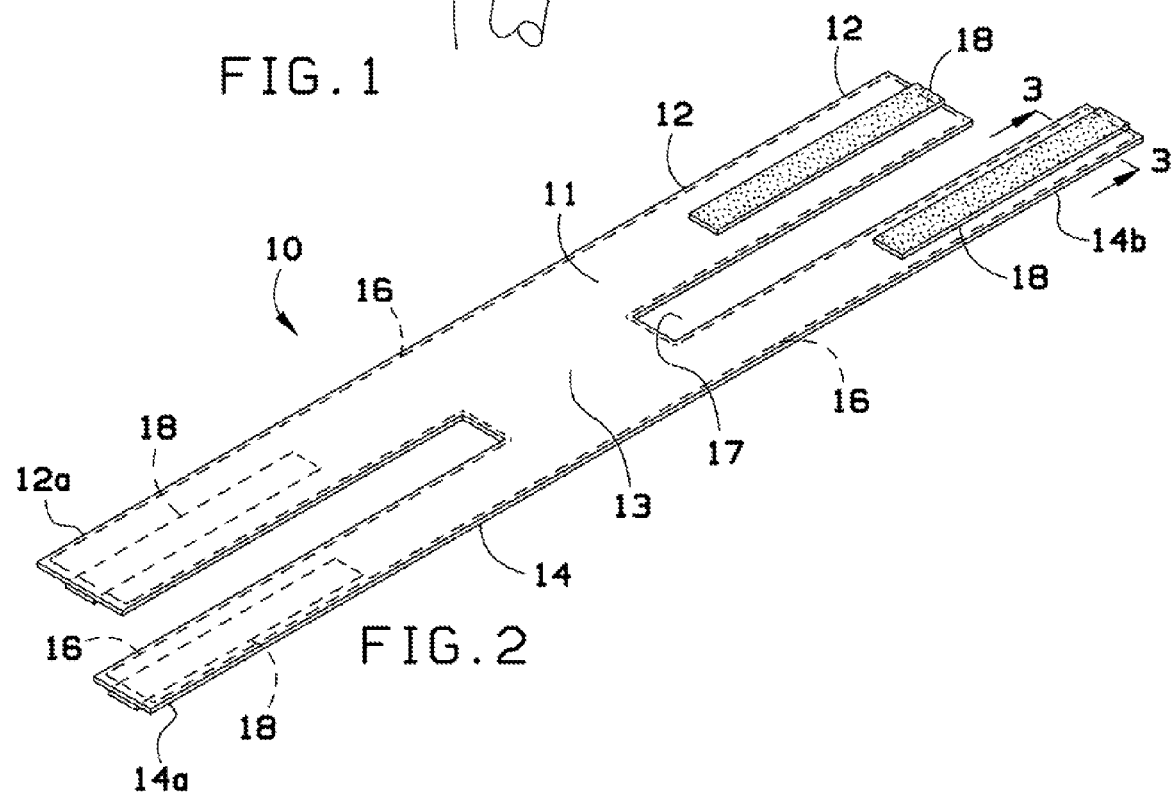
FIG. 2 illustrates a perspective front view of the chin strap assembly of FIG. 1.

FIGS. 1-3 show a chin strap assembly 10 according to the present invention. The chin strap assembly 10 may include a main body 11 having a center 13, a first strap 12 protruding from one of the sides of the center 13, and a second strap 14 protruding from the other side of the center 13. The main body 11 may have, for example, an H-shape.

The first strap 12 and the second strap 14 may be separated by a gap 17. The gap 17 may be, for example, 1.5 inches.

The main body 11 may be made of an inner layer 22 surrounded by an outer layer 20. The outer layer 20 may be made of a soft material. In some embodiments, the outer layer 20 may be made, for example, of a fluffy terry cloth or polyester. The inner layer 22 may be made of a stuffing material. In some embodiments, the inner layer 22 may be made, for example, of cotton batting.

The size of the first strap 12 and the second strap 14 may depend of the size of the patient's head.

The first strap 12 may have a first end 12a and a second end 12b. The first strap 12 may have a length of, for example, approximately 30 inches. The first end 12a and the second end 12b of the strap 12 may protrude approximately 12 inches from the edges of the center 13. The first strap 12 may have a width of, for example, 3 inches.

The second strap 14 may have a first end 14a and a second end 14b. The second strap 14 may have a length of approximately 35 inches. The first end 14a and the second end 14b of the strap 14 may protrude approximately 14.5 inches from the edges of the center 13. The second strap 14 may have a width of, for example, 2 inches.

The center 13 may have a length of, for example, 6 inches and a width of, for example, 5 inches.

An adhesive strip 18 may be secured to the first end 12a and the second end 12b of the first strap 12. In addition, adhesive strips 18 may be secured to the first end 14a and the second end 14b of the second strap 14. The adhesive strips 18 may be made of interlocking devices, for example, hook and loop fasteners, clips, or clamps. The adhesive strip 18 may be secured to the straps 12, 14 by connecting devices 16. The connecting devices 16 may be, for example, stitches, glue, or adhesive. The size of the adhesive strip 18 may depend on the size of the main body 11. The adhesive strip 18 may have, for example, a length of approximately 8 inches and a width of approximately 1 inch. The number of adhesive strips 18 may depend on the size of the main body 11. In some embodiments, there is between two and four adhesives strips 18.

The patient 28 may cover his/her mouth 26 by placing the center 13 of the main body 11 around the mouth 26, but leaving the nose (not shown) exposed. Then, the patient 28 may wrap the first end 12a and the second end 12b of the first strap 12 at the back of his/her head or neck. The patient 28 may secure the first end 12a and the second end 12b by using the adhesive strip 18. The patient 28 may pass the first end 14a and the second end 14b under the chin (not shown), lift them close to the ears 30, and then connect the first end 14a and the second end 14b of the second strap 14 on top of his/her head by using the adhesive strips 18. Then, the patient 28 may place the respiratory mask 24 as indicated by the manual of the respiratory device (not shown).

The chin strap assembly 10 may help to maintain the mouth 26 closed at the same time that it helps in positioning the chin (not shown). In addition, the chin strap assembly 10 may help prevent the air from escaping through the mouth, therefore allowing 100% of the air prescribed.

The chin strap assembly 10 may be used with any respiratory masks or nasal pillows known in the market.

It should be understood, of course, that the foregoing relates to exemplary embodiments of the invention and that modifications may be made without departing from the spirit and scope of the invention as set forth in the following claims.

What is claimed is:

1. A chin strap assembly comprising:
    a main body having a center sized to substantially completely cover a mouth of a patient, a first strap protruding from a first side of the center, and a second strap protruding from a second side of the center;
    wherein the first and second straps each have first and second ends, the chin strap assembly having a first surface and a second surface opposite the first surface;
    wherein the first ends of the first and second straps each have an adhesive strip located on the first surface of the chin strap assembly, and the second ends of the first and second straps each have an adhesive strip located on the second surface of the chin strap assembly;
    wherein the first strap and the second strap are separated by a gap;
    wherein the first strap is configured to reach behind the patient's head when the center is placed to cover the mouth, and the second strap is configured to reach over the top of the patient's head and to brace the center against the patient's chin.

2. The chin strap assembly according to claim 1, wherein the main body has an H-shape.

3. The chin strap assembly according to claim 1, wherein the adhesive strips are hook and loop fasteners.

4. The chin strap assembly according to claim 1, wherein the main body is made of an inner layer surrounded by an outer layer and the outer layer is made of a soft material and the inner layer is made of a stuffing material.

5. The chin strap assembly according to claim 4, wherein the outer layer is made of fluffy terry cloth or polyester and wherein the inner layer is made of cotton batting.

6. The chin strap assembly according to claim 1, wherein said second strap is formed with a given width sufficient to substantially cover the patient's ears.

7. A method for treating a sleep apnea patient comprising the step of:
    covering a mouth of the patient with a chin strap assembly including a main body having a center, a first strap protruding from a first side of the center, and a second strap protruding from a second side of the center; wherein the first strap and the second strap are separated by a gap; wherein the main body is made of an inner layer surrounded by an outer layer; wherein the outer layer is made of a soft material and the inner layer is made of a stuffing material;
    wrapping the first strap to a back of a head of the patient;
    passing the second strap under a chin of the patient, then lifting the second strap to cover the ears of the patient, and then securing the second strap to a top of the head of the patient; and
    placing a respiratory device over a nose of the patient.

8. The method according to claim 7, wherein the outer layer is made of fluffy terry cloth or polyester and wherein the inner layer is made of cotton batting.

9. The method according to claim 7, wherein the main body has an H-shape.

10. The method according to claim 7, further including adhesive strips secured to the first strap and to the second strap.

* * * * *